United States Patent
Uchida (10) Patent No.: US 9,875,559 B2
(45) Date of Patent: Jan. 23, 2018

(54) IMAGE PROCESSING APPARATUS AND IMAGE PROCESSING METHOD

(71) Applicant: CANON KABUSHIKI KAISHA, Tokyo (JP)

(72) Inventor: Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/168,490

(22) Filed: May 31, 2016

(65) Prior Publication Data

US 2016/0358347 A1    Dec. 8, 2016

(30) Foreign Application Priority Data

Jun. 2, 2015   (JP) .................................. 2015-112517

(51) Int. Cl.
| | |
|---|---|
| *G06K 9/00* | (2006.01) |
| *G06T 11/00* | (2006.01) |
| *A61B 3/10* | (2006.01) |
| *G01B 9/02* | (2006.01) |

(52) U.S. Cl.
CPC ............ *G06T 11/005* (2013.01); *A61B 3/102* (2013.01); *G01B 9/02091* (2013.01); *G06T 2211/412* (2013.01)

(58) Field of Classification Search
CPC ....................................................... G06T 11/00
USPC .......................................................... 382/131
See application file for complete search history.

(56) References Cited

U.S. PATENT DOCUMENTS 9,335,155 B2    5/2016 Uchida
2007/0291277 A1*  12/2007 Everett .................. A61B 3/102
                                                              356/497

FOREIGN PATENT DOCUMENTS

| EP | 2 460 463 A1 | 6/2012 | |
|---|---|---|---|
| EP | 2460463 A1 * | 6/2012 | ............... A61B 3/14 |
| EP | 2 703 771 A1 | 3/2014 | |
| JP | 2014-45869 A | 3/2014 | |
| WO | 2006/058735 A1 | 6/2006 | |
| WO | WO 2006058735 A1 * | 6/2006 | ............... A61B 3/12 |

OTHER PUBLICATIONS

Oct. 14, 2016 European Search Report corresponding to European Patent Application No. 16172093.3.

* cited by examiner

*Primary Examiner* — Gregory F Cunningham
(74) *Attorney, Agent, or Firm* — Fitzpatrick, Cella, Harper & Scinto

(57) ABSTRACT

An image processing apparatus includes an acquiring unit that acquires a plurality of pixel value rows aligned in a depth direction of an object to be measured based on interference light obtained by causing return light of scanned measurement light from the object to be measured and reference light corresponding to the measurement light to interfere with each other. A forming unit forms a two-dimensional image based on pixel values selected in accordance with a predetermined selection criterion from the plurality of pixel value rows, one of the pixel values being selected from one of the plurality of pixel value rows. In addition, a setting unit sets a selection range which is a range in the depth direction for selecting the pixel values in the plurality of pixel value rows, and a criterion changing unit changes the predetermined selection criterion in accordance with the set selection range.

20 Claims, 9 Drawing Sheets

IMAGE PROCESSING APPARATUS AND IMAGE PROCESSING METHOD

BACKGROUND OF THE INVENTION

Field of the Invention

The present invention relates to an image processing apparatus and an image processing method for acquiring a two-dimensional image from information on a tomographic image acquired by optical interference.

Description of the Related Art

An image acquiring apparatus that performs optical coherence tomography (OCT) utilizing an interference phenomenon of multi-wavelength light (hereinafter referred to as "OCT apparatus") has been known. The OCT apparatus is used for obtaining, for example, information on organs with an endoscope and information on a retina with an ophthalmologic apparatus, and the application thereof to human bodies is expanding. In particular, the OCT apparatus applied to an eye is becoming an indispensable apparatus as ophthalmologic instrument for a specialist of retina in the outpatient field.

The OCT apparatus is capable of irradiating a sample with measurement light having low coherence and measuring backscattered light from the sample through use of an interference system, to thereby acquire an image. When the OCT apparatus is applied to an eye, the OCT apparatus can photograph a tomographic image of an eye to be inspected with high resolution by scanning the eye to be inspected with the measurement light.

Further, there has been known a technology of forming a two-dimensional image of a fundus viewed from the front in a pseudo manner (hereinafter referred to as "two-dimensional image") from a plurality of tomographic images. In a method of forming a two-dimensional image, a pixel value is selected based on an order of a magnitude of pixel values from pixel value rows in a depth direction acquired by one A-scan. Then, the selected pixel value is obtained with respect to all the A-scans, to thereby form a two-dimensional image similar to a planar image of a retina (Projection image) only with tomographic images (Japanese Patent Application Laid-Open No. 2014-45869).

Further, in Japanese Patent Application Laid-Open No. 2014-45869, there is also described a method of forming a two-dimensional image regarding a predetermined layer of a retina in the case of selecting the predetermined layer. In this method, a pixel value is selected based on an order of a magnitude of pixel values from pixel value rows within the layer, to thereby form a two-dimensional image.

All the pixel value rows in a depth direction of a retina and pixel value rows within a range including a predetermined layer in the depth direction are significantly different from each other in ratio of an object to be measured in the pixel value rows. Therefore, when a pixel value is selected based on the same criteria in the case of selecting one pixel value from all the pixel value rows in the depth direction and in the case of selecting one pixel value from the pixel value rows within the predetermined range, a satisfactory two-dimensional image may not be acquired.

Further, for example, when an attempt is made to acquire a two-dimensional image of a layer having a lesion, a pixel value corresponding to a tissue influenced by the lesion may be significantly different from that of a surrounding portion. When the same criteria are used in this case, there is a risk in that a pixel value corresponding to the lesion may be deleted.

SUMMARY OF THE INVENTION

The present invention has been made in view of the above-mentioned problems, and it is an object of the present invention to provide an image processing apparatus and an image processing method, which are capable of acquiring a satisfactory two-dimensional image irrespective of conditions for obtaining information on a retina or the like in a depth direction.

In order to achieve the above-mentioned object, according to one embodiment of the present invention, there is provided an image processing apparatus, including:

an acquiring unit configured to acquire a plurality of pixel value rows aligned in a depth direction of an object to be measured based on interference light obtained by causing return light of scanned measurement light from the object to be measured and reference light corresponding to the measurement light to interfere with each other;

a forming unit configured to form a two-dimensional image based on a pixel value selected in accordance with a predetermined selection criterion from each of the plurality of pixel value rows;

a setting unit configured to set a selection range of the selected pixel value in the depth direction in each of the plurality of pixel value rows; and a criterion changing unit configured to change the predetermined selection criterion in accordance with the set selection range.

According to the present invention, it is possible to acquire a satisfactory two-dimensional image irrespective of conditions for obtaining information on a retina or the like in a depth direction.

Further features of the present invention will become apparent from the following description of exemplary embodiments with reference to the attached drawings.

DESCRIPTION OF THE EMBODIMENTS

Now, an embodiment of the present invention is described with reference to the drawings. Note that, the following embodiment is not intended to limit the present invention defined in the scope of claims, and not all combinations of features described in the embodiment are essential to solving means of the present invention.

First Embodiment

Figure 1:
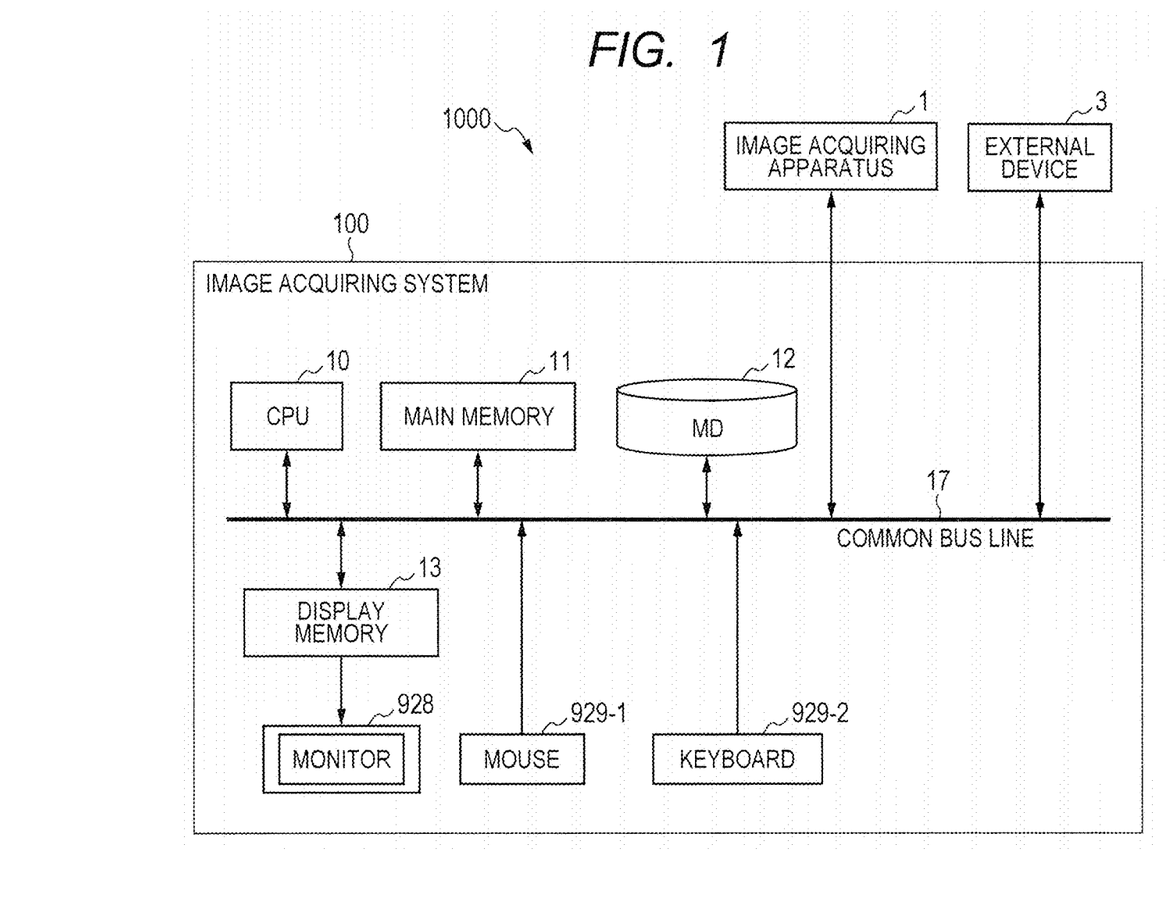
FIG. 1 is a configuration diagram of an image acquiring system including an image processing apparatus according to a first embodiment of the present invention.

FIG. 1 is a diagram for illustrating a configuration example of an image acquiring system 1000 including an image processing apparatus 100 and an image acquiring apparatus 1 to be connected to the image processing apparatus 100 according to a first embodiment of the present invention. The image processing apparatus 100 according to this embodiment includes a central processing unit (CPU) 10, a main memory 11, a magnetic disk 12, and a display memory 13. Further, the image acquiring system 1000 includes a monitor 928, a mouse 929-1, and a keyboard 929-2. The monitor 928 may include a touch panel.

The CPU 10 mainly controls the operation of each component of the image processing apparatus 100. The main memory 11 stores a control program to be executed by the CPU 10 and provides an operation area for execution of the program by the CPU 10. The magnetic disk 12 stores an operating system (OS), device drivers of peripheral devices, various application software including a program for performing, for example, a reconstruction process described later, and the like. The display memory 13 temporarily stores display data for the monitor 928. The monitor 928 is, for example, a cathode-ray tube (CRT) monitor or a liquid crystal monitor, and displays an image based on data from the display memory 13. The mouse 929-1 and the keyboard 929-2 allow a user to perform pointing input and input of characters and the like, respectively. The components described above are connected to each other through a common bus line 17 so as to communicate with each other.

The image processing apparatus 100 is connected to the image acquiring apparatus 1 through a local area network (LAN) and can obtain image data from the image acquiring apparatus 1. The mode of the present invention is not limited thereto, and the image processing apparatus 100 may be connected to the image acquiring apparatus 1 through, for example, another interface such as a universal serial bus (USB) or IEEE1394. Further, the image processing apparatus 100 may be configured to read required data through a LAN or the like from an external device 3 such as a data server configured to manage the data. Further, the image processing apparatus 100 may be connected to a storage device, such as a floppy disk drive (FDD), a CD-RW drive, an MO drive, and a ZIP drive, so as to read required data from those drives.

Figure 2:
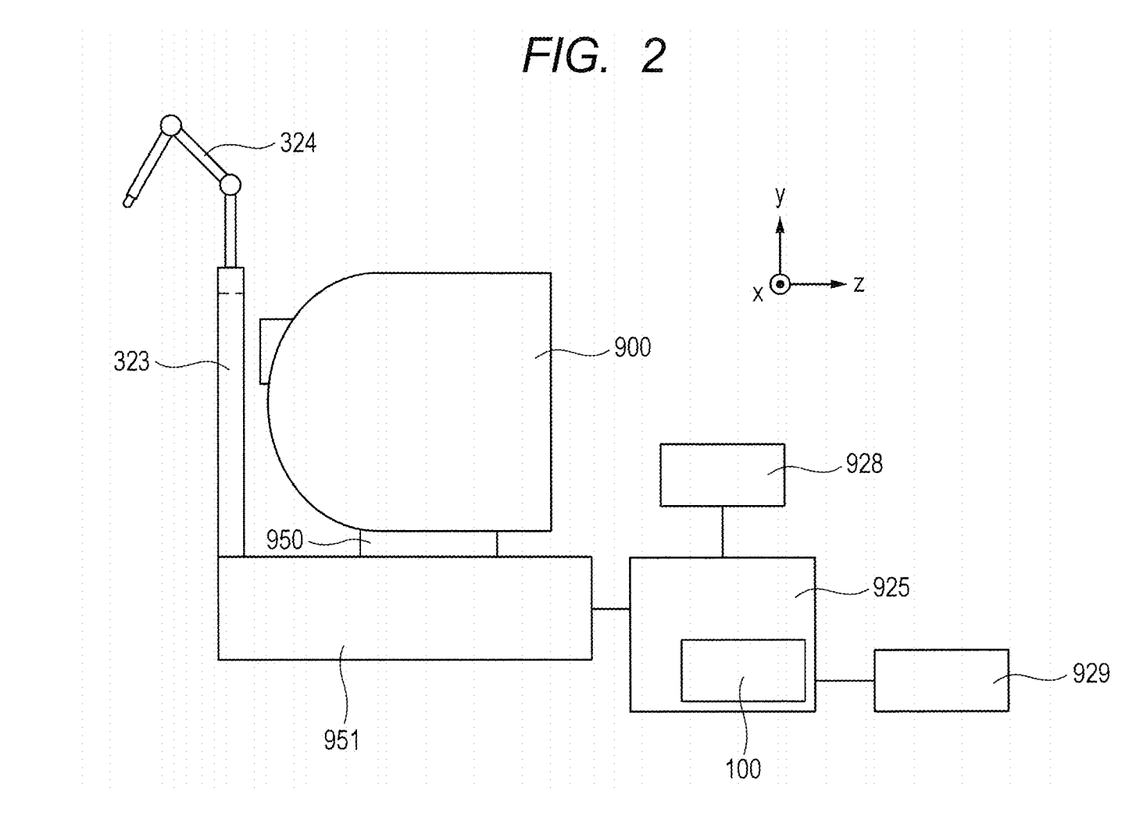
FIG. 2 is a side view of an ophthalmologic apparatus forming the image acquiring system illustrated in FIG. 1.

FIG. 2 is a side view of the image acquiring apparatus 1 constructed as an ophthalmologic apparatus with the configuration described above. The image acquiring apparatus 1 illustrated in FIG. 2 includes an external fixation target 324, a chin rest 323, a base portion 951, a stage portion 950, and an optical head 900. The optical head 900 is a measuring optical system configured to photograph an anterior ocular segment image of an eye to be inspected, and a surface image and a tomographic image of a fundus of the eye to be inspected. The stage portion 950 forms a moving portion capable of moving the optical head 900 in x, y, and z directions in FIG. 2 through use of a motor (not shown). The base portion 951 contains a spectroscope described later.

A personal computer (hereinafter referred to as "computer") 925 also serves as a control unit of the stage portion 950 and includes the image processing apparatus 100. A chin and a forehead of a subject are fixed to the chin rest 323 so that an eye (eye to be inspected) of the subject may be fixed. The external fixation target 324 is used for urging the subject to stare. Further, the image processing apparatus 100 may also be incorporated into the optical head 900 or the stage portion 950. In this case, the image acquiring apparatus 1 and the image processing apparatus 100 are integrally formed as an image acquiring apparatus.

Figure 3:
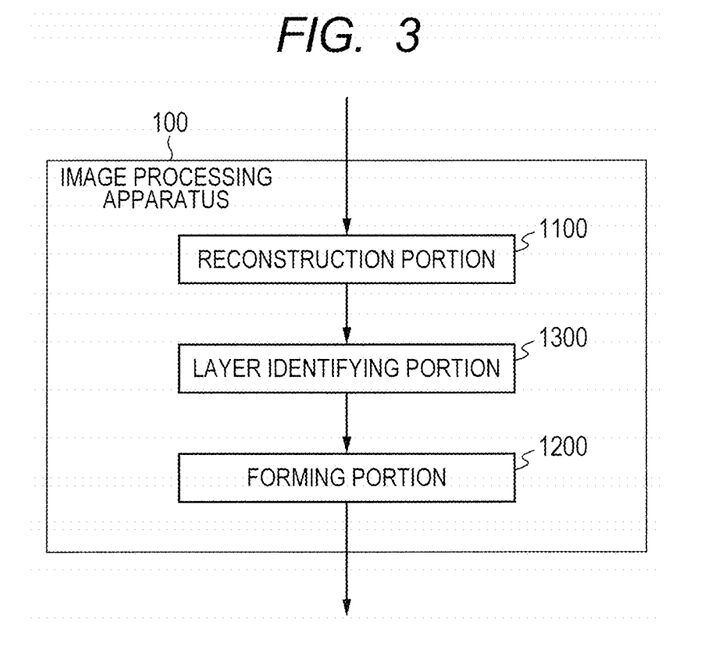
FIG. 3 is a block diagram for illustrating a configuration of the image processing apparatus according to the first embodiment of the present invention.

FIG. 3 is a block diagram for illustrating a functional configuration of the image processing apparatus 100, and the image processing apparatus 100 includes a reconstruction portion 1100, a forming portion 1200, and a layer identifying portion 1300. The reconstruction portion 1100 serves as a reconstruction unit and acquires a tomographic image within a predetermined range of an object to be measured based on interference light obtained by causing return light of measurement light from the object to be measured and reference light to interfere with each other. More specifically, the reconstruction portion 1100 subjects an output value from a sensor to wavenumber conversion and Fast Fourier Transform (FFT) to reconstruct a tomographic image (A-scan image) in a depth direction at one point on the fundus of the eye to be inspected. The forming portion 1200 serves as a forming unit configured to select a predetermined pixel from each pixel value row in the depth direction of the tomographic image acquired by the reconstruction portion 1100 for each pixel value row to form a two-dimensional image. The layer identifying portion 1300 extracts a layer structure of the object to be measured (retina) in the tomographic image acquired by the reconstruction portion 1100 to identify each layer boundary shape.

Figure 4:
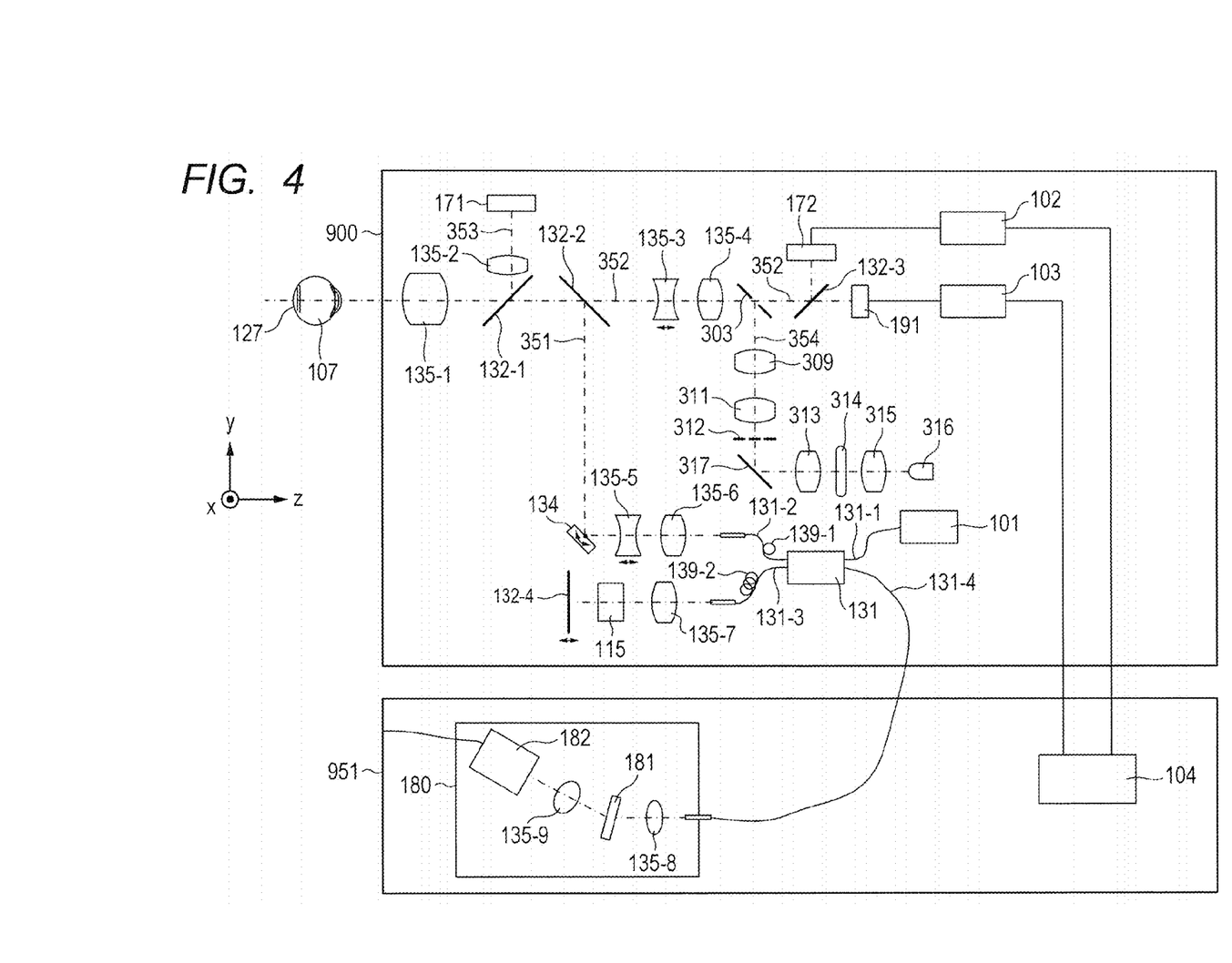
FIG. 4 is a configuration diagram of an optical system of an image acquiring apparatus provided in the image acquiring system illustrated in FIG. 1.

FIG. 4 is a diagram for illustrating a configuration of the measuring optical system and the spectroscope of the image acquiring apparatus 1. Optical elements arranged in the optical head 900 and the base portion 951 are described below.

In this embodiment, description is given below by exemplifying an eye to be inspected 107 as the object to be measured. In the optical head 900, an objective lens 135-1 is arranged to be opposed to the eye to be inspected 107. A first dichroic mirror 132-1 and a second dichroic mirror 132-2 are arranged on an optical axis of the objective lens 135-1. An optical path to the eye to be inspected 107 is branched into an optical path 353 for anterior ocular segment observation, by the first dichroic mirror 132-1 in accordance with the wavelength band. The branched optical path is further branched into an optical path 352 for a fixation target and an optical path 351 for an OCT optical system for fundus observation, by the second dichroic mirror 132-2 in accordance with the wavelength band.

A focusing lens 135-3, a lens 135-4, a perforated mirror 303, and a third dichroic mirror 132-3 are arranged on the optical path 352 for a fixation target in the stated order from the eye to be inspected 107 side. A CCD 172 is arranged in a reflection direction of the third dichroic mirror 132-3, and a fixation target 191 is arranged in a transmission direction of the third dichroic mirror 132-3. In this case, the focusing lens 135-3 is driven in a direction along the optical path 352 with a motor (not shown) so as to adjust focusing of the fixation target 191 and the CCD 172 for fundus observation.

The perforated mirror 303 is arranged between the lens 135-4 and the third dichroic mirror 132-3 and branches the optical path 352 into an optical path 354.

The optical path 354 forms an illumination optical system configured to illuminate a fundus 127 of the eye to be inspected 107. On the optical path 354, there are installed an LED light source 316 serving as an illumination light source for fundus observation to be used for positioning the eye to be inspected 107 and a stroboscopic tube 314 to be used for photographing the fundus 127 of the eye to be inspected 107. The illumination optical system includes a condenser lens 315, the stroboscopic tube 314, a condenser lens 313, a mirror 317, a ring slit 312, a lens 311, and a lens 309 arranged in the stated order from the LED light source 316 on an innermost side.

Illumination light from the LED light source 316 and the stroboscopic tube 314 is formed into a ring-like light flux by the ring slit 312 and is reflected by the perforated mirror 303 to illuminate the fundus 127 of the eye to be inspected 107. The LED light source 316 is a light source having a center wavelength of about 780 nm.

As described above, the third dichroic mirror 132-3 is arranged after the perforated mirror 303 on the optical path 352. The optical path 352 is branched into a path to the CCD 172 for fundus observation and a path to the fixation target 191 by the third dichroic mirror 132-3 in accordance with the wavelength band in the same manner as in the other dichroic mirrors.

The CCD 172 has sensitivity at the center wavelength of light emitted from the LED light source 316, which is illumination light for fundus observation, specifically about 780 nm and is connected to a CCD control portion 102. Meanwhile, the fixation target 191 emits visible light so as to urge the subject to stare and is connected to a fixation target control portion 103.

The CCD control portion 102 and the fixation target control portion 103 are both connected to a computing portion 104, and data is input to or output from the computer 925 through the computing portion 104.

A lens 135-2 and an infrared CCD 171 for interior ocular segment observation are arranged on the optical path 353 branched by the first dichroic mirror 132-1 in the stated order from the branching portion. The CCD 171 has sensitivity at the wavelength of illumination light for interior ocular segment observation (not shown), specifically about 970 nm. Further, an image split prism (not shown) is arranged on the optical path 353, and hence the distance in the z direction of the optical head 900 with respect to the eye to be inspected 107 (approaching and separation direction with respect to the eye to be inspected 107) can be detected as a split image in an anterior ocular segment observation image.

On the optical path 351, which forms an OCT optical system as described above, a configuration for actually photographing a tomographic image of the retina of the eye to be inspected 107 is arranged. More specifically, a configuration for obtaining an interference signal for forming a tomographic image is arranged. An XY scanner 134, a focusing lens 135-5, and a lens 135-6 are arranged on the optical path 351 in the stated order from the second dichroic mirror 132-2, and measurement light is supplied from the end portion of an optical fiber 131-2 to the optical path 351.

The XY scanner 134 is used for scanning the fundus 127 with the measurement light. The XY scanner 134 is illustrated as a single mirror but performs scanning in two directions of X and Y axes. The focusing lens 135-5 is driven along the optical path 351 with a motor (not shown) so as to adjust focusing of light from a light source 101, which is emitted from the end portion of the optical fiber 131-2 described later, onto the fundus 127. Further, through the adjustment of focusing, the light beams from the fundus 127 are simultaneously formed into a spot shape to enter a tip end of the optical fiber 132-2.

Next, configurations of an optical path from the light source 101, a reference optical system, and the spectroscope are described.

The light source 101 is connected to an optical coupler 131 through an optical fiber 131-1. The optical coupler 131 is connected to optical fibers 131-3 and 131-4 in addition to the optical fibers 131-1 and 131-2. Those optical fibers are optical fibers in a single mode integrally connected to the optical coupler 131. Light emitted from the light source 101 is separated into measurement light and reference light by the optical coupler 131. The measurement light is guided to the optical path 351 through the optical fiber 131-2, and the reference light is guided to a reference light path described later through the optical fiber 131-3. A reference mirror 132-4, a dispersion compensation glass 115, and a lens 135-7 are arranged on the reference light path in the stated order from the innermost side of the reference light path. The dispersion compensation glass 115 is inserted into the reference light path in order to adjust the dispersion of the reference light with that of the measurement light.

The reference light having passed through the reference light path enters an end portion of the optical fiber 131-3 and is combined with the measurement light that has similarly returned to the optical coupler 131 to be guided to a spectroscope 180 through the optical fiber 131-4. The components in this embodiment form a Michelson interferometer.

The measurement light illuminates the fundus 127 of the eye to be inspected 107 to be observed through the optical path of the OCT optical system described above, and reaches the optical coupler 131 through the same optical path due to reflection and scattering by the retina as described above. Meanwhile, the reference light reaches the reference mirror 132-4 through the optical fiber 131-3, the lens 135-7, and the dispersion compensation glass 115 and is reflected from the reference mirror 132-4. Then, the reference light returns through the same optical path to reach the optical coupler 131.

The optical coupler 131 combines the measurement light with the reference light to form interference light. In this case, interference occurs when an optical path length of the measurement light and an optical path length of the reference light become substantially equal to each other. The reference mirror 132-4 is held so as to be adjustable in an optical axis direction by a motor and a drive mechanism (not shown) and is capable of adjusting the optical path length of the reference light to that of the measurement light varying depending on the eye to be inspected 107. The interference light is guided to the spectroscope 180 through the optical fiber 131-4.

Further, a polarization adjusting portion 139-1 is provided for the measurement light in the optical fiber 131-2. A polarization adjusting portion 139-2 is also provided for the reference light in the optical fiber 131-3. Those polarization adjusting portions each have a part in which the optical fiber is looped several times. This looped part is rotated about the longitudinal direction of the fiber to twist the fiber. With this operation, the polarization state of each of the measurement light and the reference light can be adjusted and matched to each other. In this apparatus, the polarization states of the measurement light and the reference light are adjusted to be fixed in advance.

Next, the spectroscope 180 is described. The spectroscope 180 includes a lens 135-8, an imaging lens 135-9, a diffraction grating 181, and a line sensor 182. The interference light emitted from the optical fiber 131-4 is substantially collimated through the lens 135-8 and dispersed by the diffraction grating 181 to form an image on the line sensor 182 by the imaging lens 135-9. The output from the line sensor 182 is input to the personal computer 925.

Next, the periphery of the light source 101 is described. As the light source 101, a super luminescent diode (SLD) is used, which is a typical low coherent light source. Light emitted from the light source 101 has a central wavelength of 855 nm and a wavelength band width of about 100 nm. In this case, the band width influences a resolution in an optical axis direction of a tomographic image to be acquired, and hence, is an important parameter. Further, although the SLD is selected as a type of the light source, the type of the light source 101 is not particularly limited as long as the light source is capable of emitting low coherent light, and amplified spontaneous emission (ASE) or the like may also be used. Considering the measurement of an eye, near-infrared light is suitable for the central wavelength. Further, it is desired that the central wavelength be a shortest possible wavelength because the central wavelength influences a resolution in a lateral direction of a tomographic image to be acquired. For both the reasons, the central wavelength is set to 855 nm.

Although the Michelson interferometer is used as an interferometer in this embodiment, a Mach-Zehnder interferometer may be used. It is desired that the Mach-Zehnder interferometer be used in the case where an optical amount difference between the measurement light and the reference light is large, and the Michelson interferometer be used in the case where the optical amount difference is relatively small.

Next, a method of photographing an eye to be inspected through use of the image acquiring apparatus of the present invention is described.

First, an operator urges a patient to sit in front of the image acquiring apparatus according to this embodiment and starts photographing a surface image of the fundus 127 of the eye to be inspected 107. Light emitted from the LED light source 316 is formed into a ring-like light flux by the ring slit 312 and is reflected by the perforated mirror 303 toward the eye to be inspected 107. The reflected light illuminates the fundus 127 of the eye to be inspected 107. The light flux reflected from the fundus 127 caused by the illumination passes through the perforated mirror 303 and forms an image on the CCD 172. The reflected light of the fundus 127, which forms an image on the CCD 172, is imaged into a surface image of the fundus 127 by the CCD control portion 102 and sent to the image processing apparatus 100.

Next, the image acquiring apparatus 1 controls the XY scanner 134 to photograph a tomographic image of an intended section in the fundus 127 of the eye to be inspected 107, more specifically, to obtain brightness information in the depth direction on each position of the intended section.

The measurement light directed to the eye to be inspected 107 passes through the optical fiber 131-2 and is emitted from a fiber end thereof to enter the XY scanner 134. The measurement light deflected by the XY scanner 134 illuminates the fundus 127 of the eye to be inspected 107 via the objective lens 135-1. Then, the reflected light reflected from the eye to be inspected 107 follows an opposite path to return to the optical coupler 131.

Meanwhile, the reference light directed to the reference mirror 132-4 passes through the optical fiber 131-3 and is emitted from a fiber end thereof. Then, the reference light reaches the reference mirror 132-4 through the lens 135-7 and the dispersion compensation glass 115. The reference light reflected by the reference mirror 132-4 follows an opposite path to return to the optical coupler 131.

The measurement light and the reference light that have returned to the optical coupler 131 interfere with each other to form interference light. The interference light enters the optical fiber 131-4 and is substantially collimated by the lens 135-8 to enter the diffraction grating 181. The interference light having entered the diffraction grating 181 forms an image on the line sensor 182 by the imaging lens 135-9, thereby being capable of obtaining an interference signal at one point on the fundus 127 of the eye to be inspected 107.

An output value corresponding to an image signal having interference information obtained by a plurality of elements of the line sensor 182 is output to the image processing apparatus 100. In FIG. 4, a mode of acquiring a surface image of the fundus 127 at a time with emission light of the stroboscopic tube 314 is described. However, a surface image of the fundus 127 may be acquired by a scanning laser ophthalmoscope (SLO) that scans the fundus 127 with light emitted from a super luminescent diode (SLD) light source.

In this embodiment, the configuration of the OCT optical system described above corresponds to an acquiring unit configured to acquire pixel value rows aligned in the depth direction of the object to be measured based on the interference light obtained by causing the return light from the object to be measured of the measurement light used for scanning and the reference light corresponding to the measurement light to interfere with each other.

Next, a flow of an image processing method for the image processing apparatus 100 is described.

The image acquiring apparatus 1 obtains tomographic information on one point on the fundus 127 of the eye to be inspected 107. Then, the image acquiring apparatus 1 moves the irradiation position of the measurement light in the X direction by driving the XY scanner 134 serving as a scanning unit and generates interference light at another point on the fundus 127 of the eye to be inspected 107. The interference light at another point is input to the reconstruction portion 1100 via the line sensor 182. The reconstruction portion 1100 forms a tomographic image (A-scan image) in the depth direction at another point on the fundus 127 of the eye to be inspected 107 based on the input data. The position of the XY scanner 134 that has acquired an interference signal of the A-scan image and the coordinates of the A-scan image on the fundus image are stored in association with each other.

By driving the XY scanner 134 to continuously move the measurement light irradiation position in the X direction, the reconstruction portion 1100 reconstructs one tomographic image (B-scan image) in a horizontal direction of the fundus 127 of the eye to be inspected 107.

The XY scanner 134 is driven to move the measurement light irradiation position in the Y direction by a predetermined amount and then performs the scanning in the X direction described above again. In this way, the reconstruction portion 1100 reconstructs a horizontal tomographic image (B-scan image) of the fundus 127 at another position in the Y direction on the fundus 127 of the eye to be inspected 107. The XY scanner 134 is driven to repeatedly move the measurement light irradiation position in the Y direction, thereby being capable of forming a plurality of tomographic images covering a predetermined range of the fundus 127. The image acquiring apparatus 1 repeatedly forms the B-scan images while performing minute driving by a predetermined amount in the Y direction 128 times, to thereby form 128 tomographic images. Further, the reconstruction portion 1100 reconstructs (forms) a three-dimensional tomographic image from the 128 tomographic images.

Next, the forming portion 1200 forms a two-dimensional image of a retina from the tomographic images formed by the reconstruction portion 1100.

In this embodiment, the forming portion 1200 has a first mode and a second mode as an operation mode. In the first mode, a two-dimensional image is formed from pixels corresponding to the whole depth range in which brightness information for the A-scan image has been obtained. In the second mode, a two-dimensional image is formed from a predetermined depth range within the depth range in which brightness information has been obtained. A two-dimensional image formed in the first mode (hereinafter referred to as "Projection image") is also referred to as an intensity image, which is similar to the surface image of the fundus 127. Meanwhile, a two-dimensional image formed in the second mode (hereinafter referred to as "EnFace image") is a planar image formed based on any depth information on a retina and is used for visualizing a change in a retina layer structure caused by eye disease. A user can select one of the first mode and the second mode through use of at least one of the mouse 929-1, the keyboard 929-2, or the touch panel. For example, the user can select a mode by clicking one of a graphical user interface (GUI) indicating the first mode and a GUI indicating the second mode, which are displayed on the monitor 928, through use of the mouse 929-1. The monitor 928 may display the first mode and the second mode in a drop down menu so that the first mode and the second mode can be selected.

Figure 5:
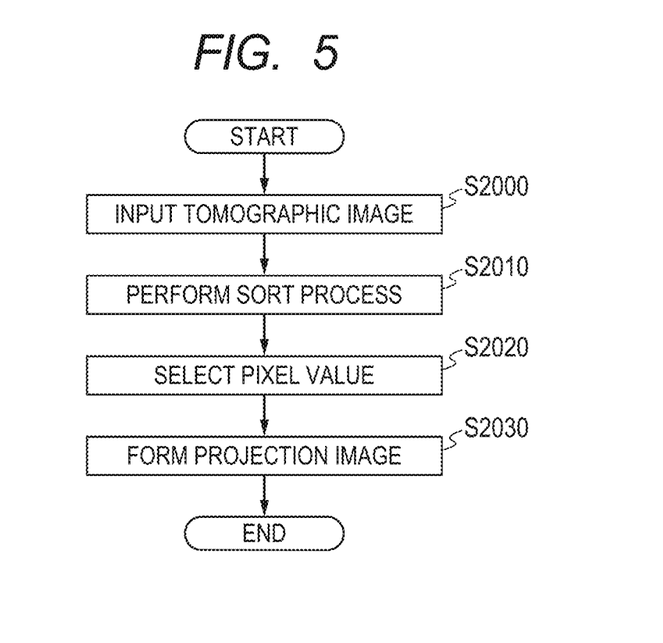
FIG. 5 is a flowchart for illustrating a flow of formation of a two-dimensional image in a first mode according to the first embodiment of the present invention.

The process of forming the Projection image in the first mode is described below with reference to FIG. 5. As described above, the tomographic image formed by the reconstruction portion 1100 is input to the forming portion 1200 (S2000).

Figure 6:
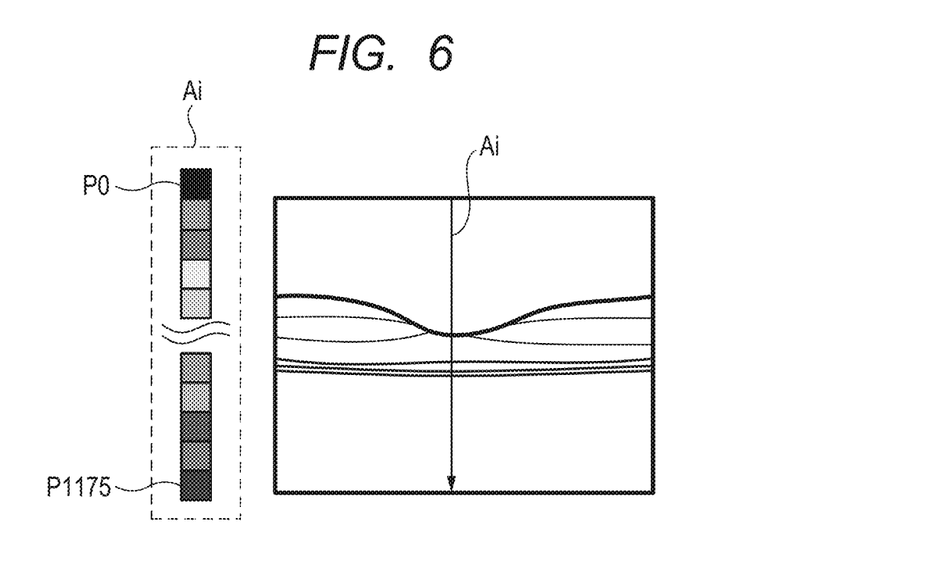
FIG. 6 is an explanatory view for illustrating a pixel value row of an A-scan image.

The A-scan image is a tomographic image in the depth direction at one point on the fundus 127 of the eye to be inspected 107 and is formed of a plurality of pieces of brightness information in the depth direction as illustrated in FIG. 6.

A two-dimensional tomographic image of FIG. 6 is a collection of A-scan images. The two-dimensional tomographic image may be a B-scan image or may indicate a cross-section of a tomographic image reconstructed three-dimensionally. As is understood from FIG. 6, the tomographic image includes a retina region and the other portions. The retina region is, for example, a region interposed between ILM and RPE.

For example, the line sensor 182 having 2,048 pixels is used in the image acquiring apparatus 1 according to this embodiment. In each A-scan image Ai after FFT, a pixel value row is formed of 1,176 pixel values. Herein, P0 denotes a value of a pixel value serving as brightness information on a shallowest portion in the depth direction with the density of a color, and P1175 denotes a pixel value serving as brightness information on a deepest portion in the depth direction. In the case of acquiring a planar image from the A-scan images, the image acquiring apparatus 1 selects and extracts one piece of brightness information from the plurality of pieces of brightness information. A pixel value corresponding to the extracted brightness information is defined as a representative intensity signal of one point on the fundus 127 of the eye to be inspected 107 from which the A-scan image has been obtained. That is, one pixel value is selected from 1,176 pixel values obtained by A-scan.

Here, the forming portion 1200 may be configured to process the tomographic image, which is acquired from the external device 3 and reconstructed, to form a Projection image. In this case, it is preferred that the brightness information and the like be received directly from a data acquiring portion (not shown) without using the reconstruction portion 1100.

Figure 7:
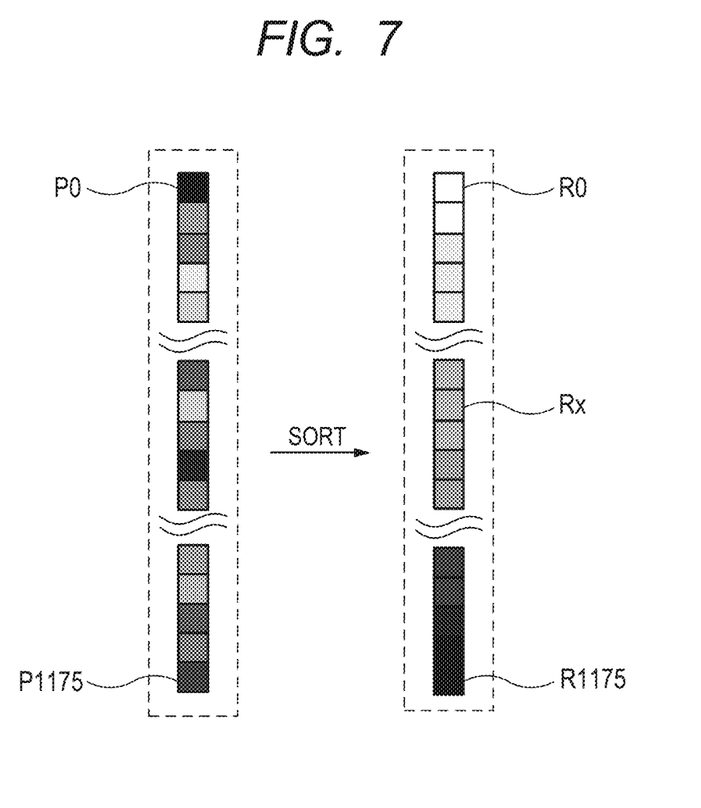
FIG. 7 is an explanatory view for illustrating an example of sorting of pixel values.

The forming portion 1200 sorts brightness information on a corresponding tomographic image in the descending order of brightness for each A-scan, as illustrated in FIG. 7. That is, pixel values are ranked based on the magnitude relationship between the pixel values for each pixel value row of 1,176 pixel values, and the pixel values are sorted (sort process) (S2010). In FIG. 7, R0 denotes a pixel having highest brightness information as a pixel value, and R1175 denotes a pixel having lowest brightness information as a pixel value. The brightness represents the intensity of interference, and hence the pixel value also corresponds to the intensity of interference. The forming portion 1200 also selects a pixel Rx at a predetermined rank in the sorted pixel value row. In this case, the pixel at the predetermined rank refers to a pixel positioned at an x-th position from the leading end after sorting in the descending order of brightness information.

When a Projection image is formed in the first mode, a pixel value at a predetermined rank is selected from a total of 1,176 pixel values included in the A-scan image. When a tomographic image of a retina is acquired, the ratio of the object to be measured (retina) in the A-scan image is about 20%. That is, about 20% of a total of 1,176 pixels forming the A-san image corresponds to pixels in a bright retina portion and the remaining about 80% corresponds to dark pixels except the object to be measured. Therefore, in the case of acquiring average brightness of a retina, it is desired that x be a pixel positioned at a higher rank than that of a half of a total number of pixels. Specifically, in the case of using the A-scan image formed of a pixel value row including a total of 1,176 pixels, a pixel at a 118-th position from the leading end, which corresponds to the position in the top 10%, is selected as the pixel Rx at a predetermined rank (S2020).

The forming portion 1200 selects the pixel Rx corresponding to the position in the top 10% with respect to all the A-scan images and forms a Projection image through use of those pixel values (S2030).

The Projection image is an image similar to the surface image of the fundus 127 acquired by the CCD 172 or the fundus image acquired by another fundus camera or an SLO, and enables visualization of the fundus surface in a pseudo manner. Further, only effective information is selectively obtained from the plurality of pieces of brightness information, and hence a suitable surface image can be acquired independently of noise components included in the A-scan image and the dark region having low intensity of interference.

Herein, an example is described in which the Projection image is formed by the forming portion 1200 after the whole data is reconstructed by the reconstruction portion 1100. However, a tomographic image reconstructed for each A-scan may be successively sent to the forming portion 1200, or a tomographic image reconstructed for each B-scan may be successively sent to the forming portion 1200.

Figure 8:
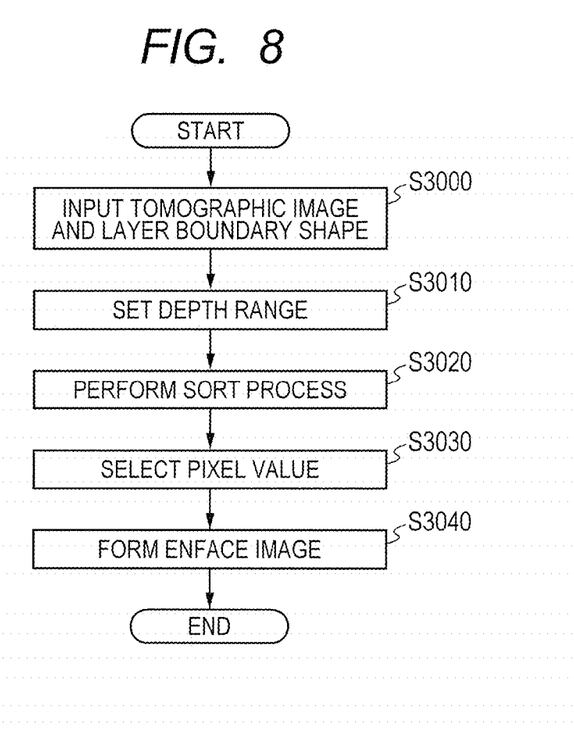
FIG. 8 is a flowchart for illustrating a flow of formation of a two-dimensional image in a second mode according to the first embodiment of the present invention.

Next, a process of forming an EnFace image in the second mode is described with reference to FIG. 8.

The layer identifying portion 1300 extracts a layer structure (layer boundary) of a retina from a two-dimensional tomographic image and specifies each layer boundary shape. As the layer boundary shape specified in this case, there are given ILM (retina-corpus vitreum boundary), an NFL/GCL boundary, a GCL/IPL boundary, an IPL/INL boundary, an IS/OS line, RPE, BM, and the like. In general, the shape of RPE or an estimated RPE (BM) is used in most cases in the EnFace image, but any shape obtained by image analysis, such as a cornea shape, may be used. The specified layer boundary shape is input to the forming portion 1200 together with the tomographic image (S3000). In this case, the forming portion 1200 may be configured to form an EnFace image through use of the layer boundary shape and the tomographic image acquired by the acquiring portion (not shown) from the external device 3. In this case, the forming portion 1200 directly receives input from the acquiring portion 2000 without using the reconstruction portion 1100 and the layer identifying portion 1300.

Figure 9A:
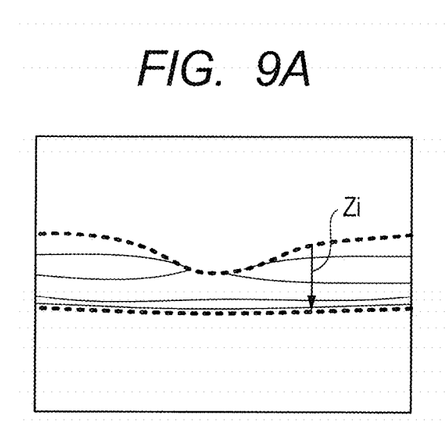
FIG. 9A and FIG. 9B are each an explanatory view for illustrating a setting example of a depth range.
Figure 9B:
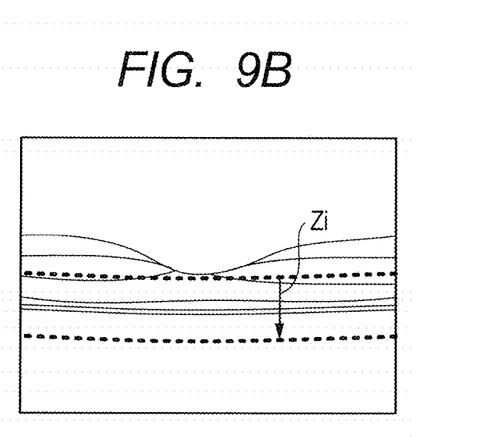

The forming portion 1200 sets a part of the pixel value row as a depth range Zi for forming an EnFace image in each A-scan image forming the tomographic image, based on the input layer boundary shape. In the case of acquiring an EnFace image of the whole retina layer, the depth range Zi from ILM to RPE is set as illustrated in FIG. 9A. Further, for example, when edema or the like in the vicinity of RPE is observed, the depth range Zi may be set by arranging two lines each having an estimated RPE shape so as to interpose the RPE therebetween at an equal distance in upper and lower directions as illustrated in FIG. 9B.

Further, the two lines for setting the depth range Zi may also be moved in upper and lower directions with the mouse 929-1 or the like. In this case, when one line having the estimated RPE shape is set on the RPE, and another line is arranged under a choroid membrane, the depth range Zi for acquiring an EnFace image of the choroid membrane can also be set. In this embodiment, when the selection range of a pixel value in the depth direction is set, the depth range is set through use of a display mode illustrated in FIG. 9A or the like in a display unit. However, the display mode for setting the depth range is not limited thereto, and various display modes, such as clicking and selecting each layer boundary with a cursor, can be used. Display in the display mode is performed with a module that serves as a display control unit in the computer 925. For example, when the user selects two layer boundaries in the tomographic image illustrated in FIG. 9A by clicking or the like, a region interposed between the two selected layer boundaries is set as the depth range Zi. The layer boundary selected by the user through use of clicking or the like may be displayed as a layer boundary superimposed on the tomographic image or a layer boundary included in the tomographic image itself.

Further, the depth range Zi can also be set without using the layer boundary shape. For example, in order to acquire an Enface image of corpus vitreum, a range from an upper end portion to an ILM boundary of the tomographic image can be set as the depth range Zi. Further, two straight lines are set at any depth positions of the tomographic image, and a range between the two straight lines can also be set as the depth range Zi.

Then, the forming portion 1200 sets the depth range Zi with respect to all the A-scan images Ai (S3010). The forming portion 1200 forms an EnFace image based on the set depth range. That is, a module serving as a setting unit in the forming portion 1200 sets, as the selection range, a part of each pixel value row in the depth direction as the depth range Zi.

As described above, in each A-scan image Ai, a pixel value row is formed of 1,176 pixel values. The forming portion 1200 acquires only a pixel value corresponding to the depth range based on the depth range Zi set with respect to each A-scan image Ai, and forms a pixel value row within the depth range Zi. Description is now given below assuming that, for example, 192 pixel values are included in a pixel value row within the depth range.

The forming portion 1200 ranks pixel values based on the magnitude relationship between the pixel values in a pixel value row within the depth range set for each A-scan, and sorts the pixel values (S3020). Then, the forming portion 1200 selects a pixel Rx at a predetermined rank. The pixel at the predetermined rank in this case refers to a pixel positioned at an x-th position from the leading end after sorting in the descending order of brightness information.

When an EnFace image is formed in the second mode, a pixel value at a predetermined rank is selected from a total of 192 pixel values included within the set depth range. When the depth range is set in an A-scan image, the ratio of a target region (for example, a retina that is an object to be measured) within the depth range is about 100%. This is because, when an EnFace image is formed, the depth range is set so that only the target region is included. Therefore, in the case of obtaining average brightness of the target region, it is not appropriate that x be positioned in the top 10% that is the same position as in the case of acquiring a Projection image, and it is desired that x be positioned substantially in the top 50% of a total number of pixels. Specifically, in the case of using a pixel value row including a total of 192 pixels, a pixel at an 81st position from the leading end, which corresponds to the position in the top 50%, is selected as the pixel Rx at a predetermined rank (S3030).

The forming portion 1200 selects the pixel Rx corresponding to the position in the top 50% from the pixel value row within the depth range Zi with respect to all the A-scan images and forms an EnFace image through use of those pixel values (S3040).

In the foregoing, when the EnFace image is formed, a pixel corresponding to the position in the top 50% is selected from the pixel value row within the depth range. However, the present invention is not limited to the pixel at the position in the top 50%. The predetermined rank can also be set in accordance with a brightness distribution (histogram) of pixel value rows, and the predetermined rank can also be changed in accordance with the ratio of the target region within the depth range. For example, when the predetermined rank is set in accordance with the brightness distribution (histogram) of the pixel value rows, which top percent position is used for selecting a pixel can be changed in accordance with the ratio of the retina included within the depth range. With such a configuration, an appropriate pixel is selected in accordance with the ratio of the retina included in the image, and hence, a satisfactory EnFace image can be formed irrespective of the difference in retina thickness of patients. For example, the layer identifying portion 1300 extracts ILM and RPE from a tomographic image and identifies a region interposed between the ILM and the RPE as a region of the retina. That is, the layer identifying portion 1300 obtains coordinates of the region of the retina in the tomographic image. Meanwhile, the forming portion 1200 obtains coordinates of the depth range Zi designated by the user. Then, the forming portion 1200 obtains coordinates of the region of the retina in the tomographic image from the layer identifying portion 1300 and compares the obtained coordinates to the coordinates of the depth range Zi, thereby being capable of calculating the ratio of the retina within the depth range Zi. That is, the forming portion 1200 can calculate the ratio of the target region included in the pixel value row. Based on this ratio, the forming portion 1200 can automatically change which top percent position is used for selecting a pixel.

The forming portion 1200 selects a pixel at a higher position as the ratio of the retina included within the depth range Zi is smaller. In other words, the forming portion 1200 selects a pixel at a lower position as the ratio of the retina included within the depth range Zi is larger. That is, the forming portion 1200 that is an example of a criterion changing unit that changes a rank of a pixel value to be used for forming a two-dimensional image in accordance with the ratio of the target region included in a pixel value row in the second mode.

The forming portion 1200 may calculate the ratio of the retina for each A-scan image to change which top percent position is used for selecting a pixel for each A-scan image, or may change which top percent portion is used for selecting a pixel based on an average value of the ratios of the retina in a plurality of A-scan images. Further, also in the first mode, the forming portion 1200 may change which top percent position is used for selecting a pixel in accordance with the ratio of the retina included in the A-scan image.

It is preferred that a change of a predetermined selection criterion in accordance with the set selection range, which is described as a predetermined rank in this embodiment, be made depending on the features of an eye of each patient, which are herein exemplified as the ratio of the retina. Further, such change may also be made based on the conditions arbitrarily selected from data on an individual patient stored in advance. In this case, the process is executed with a module that serves as the criterion changing unit in the image processing apparatus 100. Further, the criterion may be changed, for example, by determining whether a value of the ratio of the retina is more than a threshold value or not, or in accordance with input, an instruction, or the like of the operator.

The EnFace image can be acquired as images of various forms depending on the setting of the depth range, unlike the surface image of the fundus 127 acquired by the CCD 172. A two-dimensional image is formed only with information within a particular depth range, and hence the structure of the object to be measured within the depth range and a change in the structure can be remarkably visualized.

Figure 10:
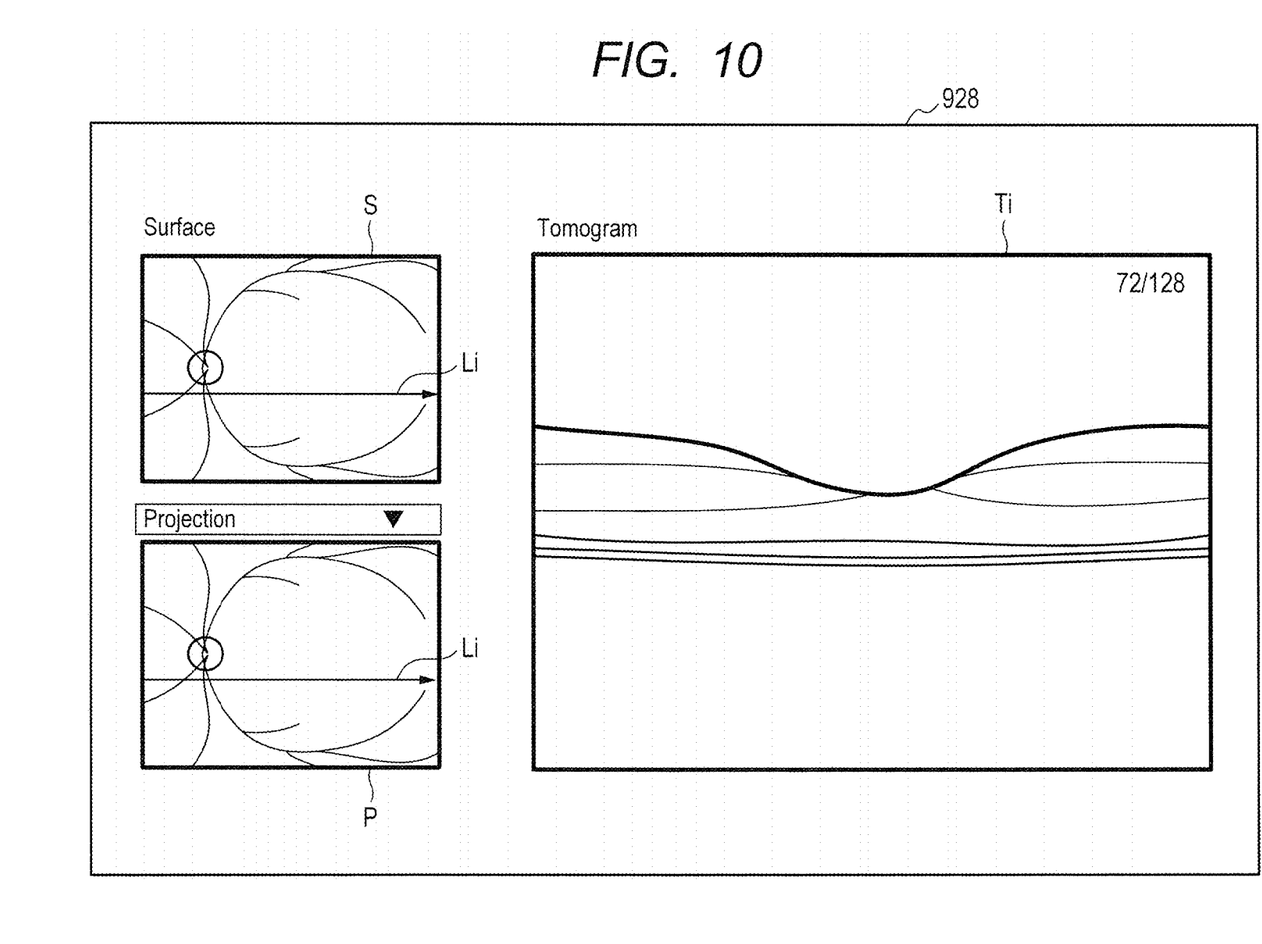
FIG. 10 is a view for showing a display example of a tomographic image and a two-dimensional image in the image acquiring system illustrated in FIG. 1.
Figure 11:
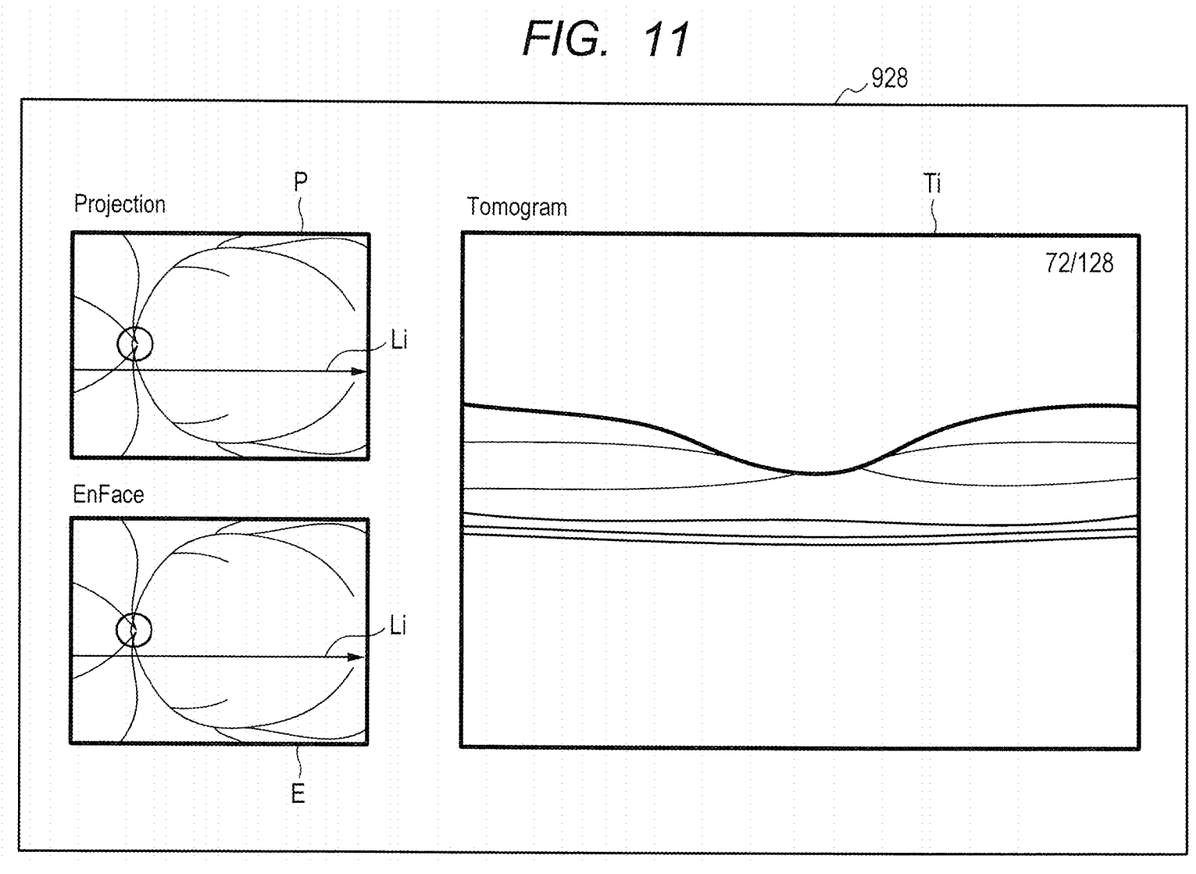
FIG. 11 is a view for showing a display example of a Projection image and an EnFace image in the image acquiring system illustrated in FIG. 1.

Next, the image acquiring apparatus 1 according to this embodiment displays the formed surface image, tomographic image, Projection image, and EnFace image of the fundus 127 on the monitor 928. As shown in FIG. 10, a surface image S, a tomographic image Ti and a Projection image P of the fundus 127 are displayed on the monitor 928 so as to be arranged next to each other. Further, an acquiring position Li of the tomographic image Ti is displayed so as to be superimposed on the Projection image P and the surface image S. The display of the Projection image P can be switched to an EnFace image E by a switching unit (not shown). Alternatively, as shown in FIG. 11, the tomographic image Ti, the Projection image P, and the EnFace image E can also be displayed on the monitor 928 so as to be arranged next to each other.

In the image processing apparatus 100 according to this embodiment, 128 tomographic images are formed. However, the tomographic image Ti (i=0 to 128) serving as one selected cross-section or a sectional image of the tomographic image Ti that is reconstructed three-dimensionally (in this case, an arbitrary number i is changed) is displayed on the monitor 928. The operator can switch and display the tomographic image to be displayed by operating the mouse 929-1 and the keyboard 929-2. In this case, when the tomographic image Ti is switched, the display position of the acquiring position Li of the tomographic image Ti to be displayed on the Projection image P, the EnFace image E, and the surface image S is also updated. With this, the operator can easily know to which position on the fundus 127 of the eye to be inspected 107 the displayed tomographic image Ti corresponds.

When the acquiring position Li is placed on the EnFace image E, a change in structure of the object to be measured within the particular depth range and the tomographic image Ti can also be observed while the change in structure and the tomographic image Ti are compared to each other.

In this embodiment, the Projection image and the EnFace image of the retina are formed based on the tomographic image of the fundus of the eye to be inspected. However, the Projection image and the EnFace image of an anterior ocular segment may be formed based on the tomographic image of an anterior ocular segment of the eye to be inspected.

The forming portion 1200 configured to form the Projection image and the EnFace image described above forms a two-dimensional image based on a pixel value selected from each of a plurality of pixel value rows described above in accordance with a predetermined selection criterion in this embodiment. In this case, as the predetermined selection criterion, a criterion such as a top several percent described above is exemplified.

Further, the predetermined selection criterion is changed in accordance with the number of pixels to be used as a pixel value row in an A-scan image to be used for selecting a pixel value. In this case, how many pixel values in the depth direction may be used or which pixel values included in the range under which conditions may be used in each of the plurality of pixel value rows is determined with the module in the image processing apparatus 100, which serves as a setting unit configured to set the selection range of a pixel value to be selected. Further, a predetermined selection criterion in accordance with the set selection range is changed with the module serving as the criterion changing unit in the image processing apparatus 100.

As described above, according to the present invention, a satisfactory two-dimensional image can be acquired both in the case where a two-dimensional image is formed based on the whole information in the depth direction and in the case where a two-dimensional image is formed based on information within a predetermined range in the depth direction.

Other Embodiments

The present invention is not limited to the above-mentioned embodiments and can be variously modified or changed without departing from the spirit of the present invention. For example, in the above-mentioned embodiments, the case where an object to be inspected is an eye, in particular, a fundus of an eye has been described, but the present invention can also be applied to objects to be measured such as a skin and an organ other than an eye. In this case, the present invention has an embodiment mode as medical equipment such as an endoscope other than an ophthalmologic apparatus. Thus, it is preferred that the present invention be understood as an image processing apparatus for an inspecting apparatus exemplified by an ophthalmologic apparatus and the eye to be inspected be understood as an embodiment mode of an object to be inspected.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-112517, filed Jun. 2, 2015, which is hereby incorporated by reference herein in its entirety.

What is claimed is:

1. An image processing apparatus, comprising:
an acquiring unit configured to acquire a plurality of pixel value rows aligned in a depth direction of an object to be measured based on interference light obtained by causing return light of scanned measurement light from the object to be measured and reference light corresponding to the measurement light to interfere with each other;
a forming unit configured to form a two-dimensional image based on pixel values selected in accordance with a predetermined selection criterion from the plurality of pixel value rows, one of the pixel values being selected from one of the plurality of pixel value rows;
a setting unit configured to set a selection range which is a range in the depth direction for selecting the pixel values in the plurality of pixel value rows; and
a criterion changing unit configured to change the predetermined selection criterion in accordance with the set selection range.

2. An image processing apparatus according to claim 1, wherein the forming unit comprises:
a first mode in which the selection range includes all of the plurality of pixel value rows in the depth direction, and the two-dimensional image is formed through use of the pixel value selected based on an order of a magnitude of the pixel values and the predetermined selection criterion; and
a second mode in which a part of the pixel value row in the depth direction is set as the selection range by the setting unit, and the two-dimensional image is formed through use of the pixel value selected based on the order of the magnitude of the pixel values within the selection range and the predetermined selection criterion.

3. An image processing apparatus according to claim 2, wherein the forming unit is configured to rank the pixel values based on a magnitude relationship between the pixel values for the plurality of pixel value rows, and to form the two-dimensional image based on the predetermined selection criterion which is a predetermined rank in the pixel value row including the ranked pixel values, and
wherein the first mode and the second mode are different from each other in predetermined rank.

4. An image processing apparatus according to claim 3, wherein the criterion changing unit is configured to change the predetermined rank in accordance with a ratio of a target region included in the set selection range.

5. An image processing apparatus according to claim 3, wherein, when the pixel values are ranked by aligning the pixel values in a descending order, the predetermined rank in the first mode is higher than the predetermined rank in the second mode.

6. An image processing apparatus according to claim 1, further comprising a display unit configured to display the two-dimensional image formed by the forming unit.

7. An image processing apparatus according to claim 6, further comprising a display control unit configured to cause the display unit to display a display mode for allowing the setting unit to set the selection range when the setting unit sets the selection range of the pixel value in the depth direction.

8. An image processing apparatus according to claim 6, wherein the display unit is capable of switching and displaying the two-dimensional image in the first mode formed by the forming unit and the two-dimensional image in the second mode formed by the forming unit.

9. An image processing apparatus according to claim 6, wherein the display unit is capable of displaying the two-dimensional image in the first mode formed by the forming unit and the two-dimensional image in the second mode formed by the forming unit so as to be arranged next to each other.

10. An image processing apparatus according to claim 1, wherein the object to be measured comprises an eye.

11. An image processing method, comprising:
acquiring a plurality of pixel value rows aligned in a depth direction of an object to be measured based on interference light obtained by causing return light of scanned measurement light from the object to be measured and reference light corresponding to the measurement light to interfere with each other;
forming a two-dimensional image based on pixel values selected in accordance with a predetermined selection criterion from the plurality of pixel value rows, one of the pixel values being selected from one of the plurality of pixel value rows;
setting a selection range which is a range in the depth direction for selecting the pixel values in the plurality of pixel value rows; and changing the predetermined selection criterion in accordance with the set selection range.

12. A non-transitory storage medium having stored thereon a program for causing a computer to execute the steps comprising:
   acquiring a plurality of pixel value rows aligned in a depth direction of an object to be measured based on interference light obtained by causing return light of scanned measurement light from the object to be measured and reference light corresponding to the measurement light to interfere with each other;
   forming a two-dimensional image based on pixel values selected in accordance with a predetermined selection criterion from the plurality of pixel value rows, one of the pixel values being selected from one of the plurality of pixel value rows;
   setting a selection range which is a range in the depth direction for selecting the pixel values in the plurality of pixel value rows; and
   changing the predetermined selection criterion in accordance with the set selection range.

13. An image processing apparatus according to claim 4, wherein the object to be measured is an eye, and the target region is a retina of the eye.

14. An image processing apparatus according to claim 1,
   wherein the forming unit comprises a first mode for forming the two-dimensional image and a second mode for forming the two-dimensional image,
   wherein the selection range in the first mode is different from the selection range in the second mode,
   wherein the forming unit is configured to rank the pixel values based on a magnitude relationship between the pixel values for the pixel value row, and form the two-dimensional image based on the predetermined selection criterion which is a predetermined rank in the pixel value row including the ranked pixel values, and
   wherein the predetermined rank in the first mode is different from the predetermined rank in the second mode.

15. An image processing apparatus according to claim 14, wherein the selection range in the first mode is wider than the selection range in the second mode in the depth direction.

16. An image processing apparatus according to claim 14, wherein, when the pixel values are ranked by aligning the pixel values in a descending order, the predetermined rank in the first mode is higher than the predetermined rank in the second mode.

17. An image processing apparatus according to claim 15, wherein, when the pixel values are ranked by aligning the pixel values in a descending order, the predetermined rank in the first mode is higher than the predetermined rank in the second mode.

18. An image processing apparatus according to claim 1,
   wherein the forming unit is configured to rank the pixel values based on a magnitude relationship between the pixel values for the pixel value row, and form the two-dimensional image based on the predetermined selection criterion which is a predetermined rank in the pixel value row including the ranked pixel values, and
   wherein the criterion changing unit is configured to change the predetermined rank in accordance with a ratio of a target region included in the set selection range.

19. An image processing apparatus, comprising:
   an acquiring unit configured to acquire a plurality of pixel value rows aligned in a depth direction of an object to be measured based on interference light obtained by causing return light of scanned measurement light from the object to be measured and reference light corresponding to the measurement light to interfere with each other;
   a forming unit configured to form a two-dimensional image based on pixel values selected in accordance with a predetermined selection criterion from the plurality of pixel value rows, one of the pixel values being selected from one of the plurality of pixel value rows;
   a setting unit configured to set a selection range which is a range in the depth direction for selecting the pixel values in the plurality of pixel value rows; and
   a criterion changing unit configured to change the predetermined selection criterion in accordance with a ratio of a target region included in the set selection range.

20. An image processing apparatus according to claim 19, wherein the object to be measured is an eye, and the target region is a retina of the eye.

* * * * *